United States Patent [19]
McRae

[11] Patent Number: 5,141,717
[45] Date of Patent: Aug. 25, 1992

[54] CARBON MONITOR CONTAINING ANION EXCHANGE RESIN

[75] Inventor: Wayne A. McRae, Zurich, Switzerland

[73] Assignee: Ionics, Incorporated, Watertown, Mass.

[21] Appl. No.: 633,569

[22] Filed: Dec. 24, 1990

[51] Int. Cl.$^5$ ............................................. G01N 33/00
[52] U.S. Cl. ................................. 422/82.01; 422/82.02; 422/76; 436/145; 436/146; 436/150; 73/61.41; 210/746; 210/198.2; 324/464
[58] Field of Search .................... 422/82.01, 82.02, 70, 422/76; 210/746, 198.2, 96.1, 85, 181; 55/386; 73/19.02, 61.1 R, 61.1 C; 324/464; 436/145, 146, 150

[56] References Cited

U.S. PATENT DOCUMENTS

| | | |
|---|---|---|
| 3,864,083 | 2/1975 | Green et al. .................... 422/82.02 |
| 4,281,387 | 7/1981 | Kraft et al. ............................ 422/62 |
| 4,940,667 | 7/1990 | Goldstein et al. .................. 436/150 |

Primary Examiner—James C. Housel
Assistant Examiner—Lyle A. Alexander
Attorney, Agent, or Firm—Norman E. Saliba

[57] ABSTRACT

Apparatus for measuring the concentration of carbon compounds in water, the apparatus including a reaction zone for converting such carbon compounds to free and/or combined carbonaceous acids, a device for introducing at least a portion of the water to be analyzed as liquid or vapor into such zone, a device for contacting such acids with weakly basic anion exchange resin and a device for measuring the electrical impedance of at least a portion of such resin.

10 Claims, 3 Drawing Sheets

CARBON MONITOR CONTAINING ANION EXCHANGE RESIN

BACKGROUND OF THE INVENTION

Field of the Invention and Description of Prior Art

This invention pertains to apparatus for measuring the quantity of organic matter in water. Such matter may include volatile organics including volatile halogenated organics such as trihalomethanes ("THM's").

Prior art apparatus for measuring organic matter in water includes:

Total Oxygen Demand ("TOD") Analyzer: This apparatus uses a furnace operating at about 900° C. and containing for example Pd or Pt wool or gauze. A stream of e.g. $N_2$, He or A carrier gas containing a low level of $O_2$ passes through the furnace. The $O_2$ content of the carrier gas downstream of the furnace is measured electrochemically, e.g. by a doped $ZrO_2$ high temperature $O_2$ concentration cell. From time to time a precise droplet of water is injected automatically or by manual micro-syringe directly into the furnace and the depletion of $O_2$ in the carrier gas measured. The apparatus must be calibrated from time to time against a known standard sample. The apparatus suffers from instability of the $O_2$ concentration cell sensor and from the fact that the latter responds not to change in $O_2$ concentration but to the change in logarithm of such concentration. It responds not only to carbon compounds but also to compounds such as $NH_3$. It responds "negatively" to $NO_3-$ and dissolved $O_2$. The latter can be reduced to low levels by sparging with $N_2$, He or A for example but at the risk of loss of volatile carbon compounds.

TOD is not sufficiently sensitive at concentrations of organics of interest in potable, pure and ultrapure water. Total Carbon Analyzer ("TCA"): This apparatus also uses typically a 900° C. furnace with noble-metal wool or gauze. The gas passing through the furnace may be air though for analyses at low levels of carbon compounds in water it is preferred to use carbon-dioxide-free air or pure oxygen optionally diluted with an unreactive gas such as $N_2$, He or A. The $CO_2$ content of the gas downstream of the furnace is measured with a non-dispersive IR photometer. Again a precise droplet of water is injected from time to time into the furnace and the increase in $CO_2$ in the gas stream determined. This apparatus must also be calibrated from time to time against known samples.

A variation of the apparatus reduces the $CO_2$ to $CH_4$ with hydrogen and measures the latter by flame ionization detection. Both variations suffer also from lack of sensitivity below 1 ppm organic carbon.

Organic Carbon Analyzer ("OCA" or "TOC"): The two variations of TCA discussed above measure not only $CO_2$ from oxidation of organic carbon compounds but also from $CO_2$, $HCO_3-$ and/or $CO_3=$ (inorganic carbon") which may be present in the water. An OCA device typically comprises a TCA apparatus having a pretreatment section to remove $CO_2$, $HCO_3=$, for example by acidifying and stripping with air, $N_2$ etc.. Such pretreatment may also remove volatile organic compounds ("VOC's") including THM's, thereby potentially further degrading the sensitivity of the apparatus.

Attempts have been made to overcome the problems occasioned in the above devices from the presence of the high temperature furnaces by oxidizing the organic matter in a sample in the liquid state, promoted by U.V. light with or without added persulfate salt. The $CO_2$ produced has been detected in a variety of ways, for example:

a) the $CO_2$ is sparged out of the oxidation zone typically with air (though $O_2$, $N_2$, A, He could in principle be used) and dissolved in a known volume of ultrapure water. The change in electrical conductivity of the ultrapure water is measured from which the concentration of $CO_2$ can be calculated. However, as is well known, $CO_2$ is present in water (at least in part) as $H_2CO_3$, a very weak acid which is poorly ionized. Hence the change in conductivity of the ultrapure water receiving stream is small for low concentrations of organic carbon in the sample. Such defect may be ameliorated in part by using fairly large samples compared to the volume of receiving ultrapure water. Any strongly ionized electrolytes carried over as mist in the $CO_2$ sparging gas of course give a spurious result. In one version of the above described apparatus the sparging gas is recycled to the oxidation zone in which case an equilibrium is eventually reached between dissolved free (i.e. uncombined) $CO_2$ in the oxidation zone (at the pH pertaining therein) and in the ultrapure water. There is increased risk in this case of carry-over of strong electrolytes. To distinguish between inorganic and organic carbon compounds the sample in the oxidation zone is acidified before oxidation commences and the resulting (inorganic) $CO_2$ removed to the receiving ultrapure water by sparging. VOC's may be removed in the process. (This practice tends to mask the effects of carry-over of strong electrolytes). The apparatus is not stable and both background correction and calibration must be carried out on at least a daily basis if samples containing 1 ppm or less of organic carbon are to be analyzed FIG. 1 is a schematic representation of one embodiment of apparatus according to the above described process. The major components of the apparatus are:

the U.V. irradiation chamber 201 with a 184.9 nm U.V. light source 202 surrounded by a quartz or other 184.9 nm substantially transparent sleeve.

the measuring chamber 203 which houses a conductivity cell 204. (The latter according to the present invention preferably comprises a weakly basic anion exchange structure as more fully described below).

an eductor 205 which pulls a gas e.g. air from the irradiation chamber 201 through the measuring chamber 203.

a pump 206.

a mixed bed ion exchanger 207 to purify the water in measuring chamber 203 after each analysis.

a conductivity processing and display and/or recording module 208.

Analysis begins with closing of valves on each end of the mixed bed ion exchanger 207, de-energizing UV light source 202 and introducing a suitable volume of sample plus a small amount of e.g. phosphoric acid and optionally potassium peroxydisulfate into U.V. irradiation chamber 201. Throughout the analysis water is recirculated through the pump 206, eductor 205 and U.V. irradiation chamber 201 and a stream of suitable gas from U.V. irradiation chamber 201 through the water in the measuring chamber 203 back through the eductor 205 into U.V. irradiation chamber 201. A first conductance of conductivity cell 204 is then measured and the U.V. light source is then energized. When the conductance of conductivity cell 204 essentially reaches steady state a second conductance of such cell is measured. The difference between such first and second conductances is a measure of the organic carbon content of the above mentioned sample. (According to the improvement described herein below conductivity cell 204 is preferably a weakly basic anion exchange resin). The liquid water in measuring chamber 203 is then recirculated through mixed bed ion exchanger 207 thoroughly to deionize the water.

b) the $CO_2$ is sparged out of the oxidation zone, trapped and concentrated on a solid sorbent. The sorbent is subsequently heated rapidly and the $CO_2$ released is measured by a non-dispersive IR detector. In principle the released $CO_2$ could be catalytically hydrogenated to $CH_4$ and the latter detected by flame ionization. Inorganic and organic carbon are distinguished by acidifying and sparging the sample before the oxidation step. VOC's may be removed in the latter process. In some versions of the above described device the step of concentrating the $CO_2$ on a solid sorbent is omitted.

c) the change in electrical conductivity of the water in the oxidation zone is measured and interpreted in terms of $CO_2$ or organic carbon. The sparging step is thereby eliminated. In a variation of this method oxidation of the organics in the sample is allowed to proceed only to organic acids and not to $CO_2$. In either case the change in conductivity must be detected against the background of electrolytes initially present in the sample. Accurate results are difficult to obtain if such background conductivity is greater than about 2 microSiemens/cm ("$\mu S/cm$") i.e. about 1 ppm NaCl. Since the measurement of conductivity change is carried out in the same volume of water in which the UV promoted oxidation takes place, correction is not required for inorganic carbon. It is clear however that the presence of $HCO_3-$ (or anions of other weak inorganic acids) must buffer the dissociation of any $CO_2$ (and/or organic acid) produced by the oxidation. Further it is clear that some organics are easily and rapidly oxidized to $CO_2$ by UV promoted oxidation and that it may be difficult to limit the oxidation products to organic acids. It is equally clear that other organics are oxidized to $CO_2$ only slowly and with difficulty by UV promoted oxidation. Such devices are therefore less useful in monitoring the absolute concentration of organics in an unidentified water sample than in monitoring the hour-by-hour or day-by-day performance of a purification system on a given water source. Hydrohalic acids produced by oxidation of halogenated organics also interfere with the interpretation of the conductivity charge.

FIG. 2 is a schematic representation of one embodiment of apparatus according to the above described process. 510 represents a sample cell arranged to be connected at port 512 to a source of influent water which is to be analyzed for organic carbon. Effluent water exits at port 514. Cell 510 is divided into two main parts 516 and 518. A recess in part 516 is covered by a quartz window (or other U.V. transparent window). A liquid tight chamber 524 is formed in part 516 by gasket 522 and window 520. The conductivity of the liquid in chamber 524 is measured by means of central electrode 526 and peripheral electrode 528 (According to the improvement described herein below the concentration of carbonaceous acids is measured by means of the conductivity of weakly basic anion exchange resin, preferably shielded from the U.V. irradiation). A temperature sensor 527 may be attached to the rear of chamber 524. Electrodes 526 and 528 may be connected to an analog-digital converter 530 (or to a simple conductivity meter) and to a data processing and/or recording device 532. A U.V. lamp 534 is inserted into port 518. 536 represents a mirror. Chamber 538 is generally filled with a gas which does absorb the principal lines of lamp 534.

It is obvious that the sample of water to be analyzed by the devices mentioned immediately above (i.e. in which the conductivity after oxidation is measured in the same medium) may not be acidified and sparged to remove inorganic carbon since the added acid contributes an unacceptable background electrical conductivity and will as well suppress ionization of any $CO_2$ (or organic acids) formed in the oxidation step. (It will be understood however that owing to the nature of the detection process inorganic carbon will not interfere with the detection of organic carbon except for the buffering effect of the former mentioned above). If the sample contains halogenated organics oxidation of which is promoted by UV, then the conductivity contributed by any hydrohalo acids formed will be interpreted as a relatively very much larger concentration of $CO_2$ (or organic acid).

It will be seen from the above discussion that the problem of measuring low levels of organic compounds in water in the presence of inorganic carbon ($CO_3=$, $HCO_3-$ and $H_2CO_3$), VOC's (including volatile halogenated organics) and/or significant amounts of electrolytes has not been satisfactorily solved by methods and apparatus known in the art. In U.S. Pat. No. 4,940,667 (assigned to the same assignee as the present application and incorporated herein by reference) an improvement in the art was disclosed in which at least part of a sample of water to be analyzed is vaporized by "quiet boiling" through a high temperature oxidizing/reforming furnace which oxidizes/reforms VOC's into $CO_2$. The vaporized water and $CO_2$ formed are condensed and the electrical impedance of the thus condensed liquid is measured. The method is simple and inexpensive and, if care is taken to avoid carry-over of mist, suppresses the contribution to the electrical conductivity of the condensed sample from strongly ionized inorganic electrolytes present in the sample. (Correction may be made for any residual contribution of such electrolytes and volatile inorganic carbon by running a duplicate sample in the apparatus with the temperature of the furnace below oxidation/reforming temperatures). The method and apparatus of said application do not detect non-volatile organics however and do not distinguish between $CO_2$ formed from VOC's and hydrohalic acids formed from volatile halogenated organics. Precision of the method and apparatus depends upon measuring or controlling the fraction of the sample which is both vaporized by quiet boiling and condensed to liquid water and by substantial condensation and reflux to the quiet boiler of vapor before said vapor enters the high temperature oxidizing/reforming furnace. It goes without saying that the temperature of the impedance measuring sensor must be controlled and/or measured.

The apparatus described above as shown in FIG. 3 is taken from said U.S. Pat. No. 4,940,667. The apparatus is fabricated in whole or in part from commercial quartz, vitreous silica, pyroceram, alumina, mullite or porcelain. Chamber 41 is a receiver typically having a diameter of about 11 to 12 millimeters and a height of from about 37 to about 50 millimeters. Receiver 41 may be wrapped in Nichrome or similar heating wire held in place with a high temperature ceramic adhesive well known in the art. Water to be analyzed is introduced into receiver 41 by conduit means 42a and/or 42b. Vapor from receiver 41 passes into chamber 413 which serves the dual purpose of mist eliminator and partial condenser. In the embodiment shown in FIG. 4, chamber 413 protrudes into receiver 41 and has openings 415 to allow vapor to enter chamber 413 while minimizing the probability of liquid being entrained in case of bumping during evaporation in receiver 41. Any condensate formed in chamber 413 flows back into receiver 41 through openings 415. Such partial condensation of vapor (caused by cooling at walls of chamber 413) enriches the concentration of volatile organics (particularly volatile, less hydrophilic organics) in the water vapor passing from chamber 413 into heated zone 45. Chamber 413 may be at least partly filled with suitable foraminous packing such as glass beads 414 to encourage good contact between refluxing partial condensate and vapor rising from receiver 41 toward heated zone 45. The flow of condensed water vapor counter-current to the ascending water vapor results in enrichment of organic components more volatile than water and also in scrubbing out of mist which may form in the event of less than gentle evaporation in receiver 41. Zone 45 may be heated by Nichrome or other suitable heating wire or ribbon held in place by a ceramic adhesive well known in the art. Zone 45 is generally insulated with suitable insulating material. Zone 45 is typically heated to a temperature in the range of 450° to 1000° C. at which temperature organic components in the water vapor are oxidized (by residual oxygen in the water vapor) and/or reformed (by the water vapor per se) into carbon dioxide and other simple compounds. The rate of oxidation and/or reformation may be increased by including extended surface area (such as porous ceramics or activated porous ceramics) in Zone 45. 47 represents condensing means, appropriately cooled, and may also contain extended surface, e.g. glass beads. A condensate receiver 410 communicates with impedance measuring means 48 which according to U.S. Pat. No. 4,940,667 may be a pair of electrodes (but according to the improvement described herein below is preferably a weakly basic anion exchange resin).

By way of improvement over the above mentioned method and apparatus, the organics in a sample of water are first oxidized and at least part (preferably a controlled and/or measured fraction) of the oxidized sample is vaporized by quiet boiling and condensed, preferably with substantial reflux to the quiet boiler. Relevant apparatus is illustrated schematically in FIG. 4 in which 301 represents an entrance conduit for a liquid sample which has been oxidized (e.g. by ultraviolet irradiation with or without added oxidizing agents such as persulfate, by Fenton's reagent (hydrogen peroxide plus an iron salt), by persulfate plus a silver salt at an elevated temperature, by ozone with or without added hydrogen peroxide, by chromic acid etc.) and which has a pH preferably less than about 4.5, for example by having been adjusted with phosphoric acid. 304 represents a reboiler, heated with any suitable element 305 well known in the art. 302 represents a volatile carbonaceous acid enriching section, packed with any suitable material, e.g. glass beads, and 303 represents a volatile carbonaceous acid stripping section also packed with suitable material. (Such stripping section may be omitted under some circumstances). Distillate issuing from the top of 302 is condensed by condenser 307 and collected in receiver 308. The electrical impedance of condensed water in 308 is measured for example by high frequency coil 310 or by a pair of suitable electrodes (but according to the improvement described herein below is preferably a weakly basic anion exchange resin). Underflow from receiver 308 through conduit 311 provides reflux to the carbonaceous acid fractionator represented by 302 and 303. In one embodiment reboiler 304 is also the oxidation zone, in which case stripping section 303 may be eliminated and the water sample, added oxidant and added pH control agents (if any) introduced through 301 directly into reboiler 304. The electrical impedance of the condensed liquid is measured. The improvement effectively suppresses the contribution to the electrical conductivity of the condensed sample by inorganic electrolytes present in the sample. Hence peroxydisulfates and other oxidizing agents (e.g. iron salts plus hydrogen peroxide), buffering agents, acids can be added to the sample before or during oxidation and/or before or during quiet boiling to enhance the oxidation or for other effects useful in the analysis. The oxidizing agents can include ozone generated on site. The oxidation can be assisted by UV irradiation.

The above mentioned improvement also suppresses the interference caused by chlorine containing organics since any hydrogen chloride formed by oxidation of the latter is much less volatile than water vapor at low concentrations of hydrogen chloride.

All the above mentioned methods and apparatus which determine $CO_2$ formed from organic carbon by change in electrical conductivity or impedance caused by such $CO_2$ suffer from the poor dissociation of $CO_2$ (resp. $H_2CO_3$) in water and hence from loss of precision owing to possible contamination by strongly dissociated electrolytes. It is therefore an objective of the present invention to provide a simple, inexpensive method and apparatus for detecting $CO_2$ which is not restricted by such poor dissociation. It is also an objective to provide an apparatus and method suitable for the detection of low concentrations of organics in water particularly in potable, pure and ultrapure water, which method and apparatus avoid many of the problems of prior art apparatus and methods. These and other objectives will become apparent from the disclosure and claims below.

DESCRIPTION OF THE PREFERRED EMBODIMENTS

Figure 1:
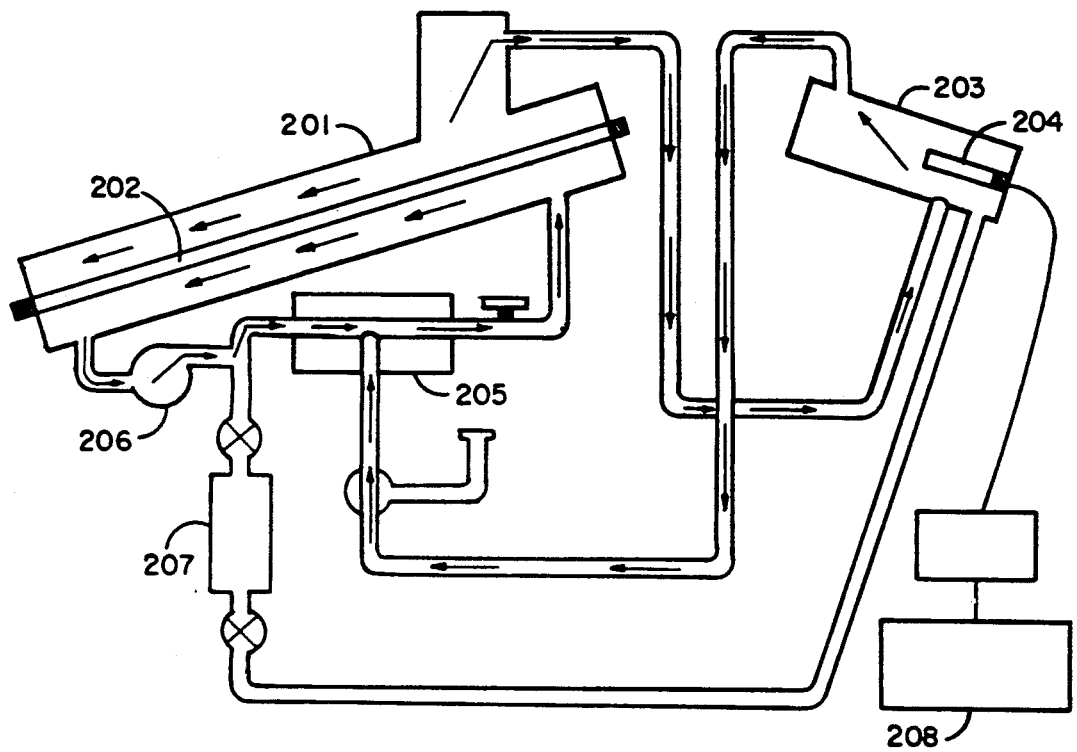
FIG. 1 is a schematic and simplified diagram of a first prior art apparatus for measuring dissolved and/or dispersed carbon compounds in water and also illustrating how such apparatus may be improved in accordance with this invention.
Figure 2:
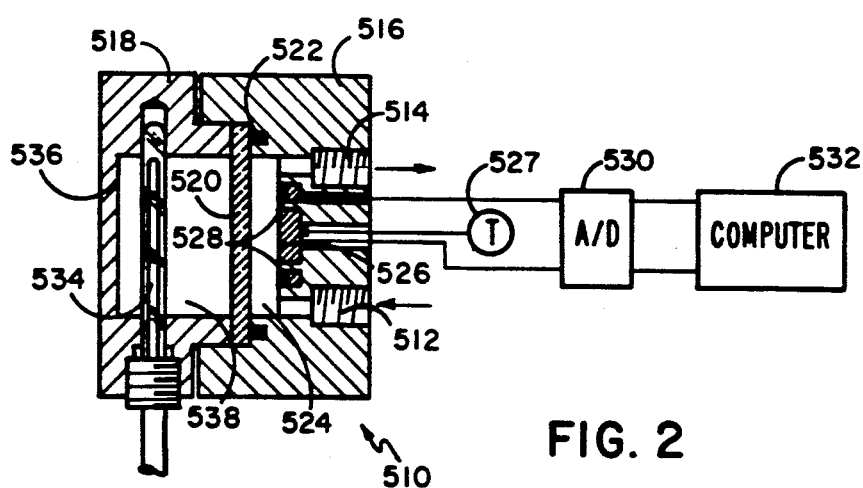
FIG. 2 is a schematic and simplified diagram of a second prior art apparatus for measuring dissolved and/or dispersed organic compounds in water and also illustrating how such apparatus may be improved in accordance with this invention.
Figure 3:
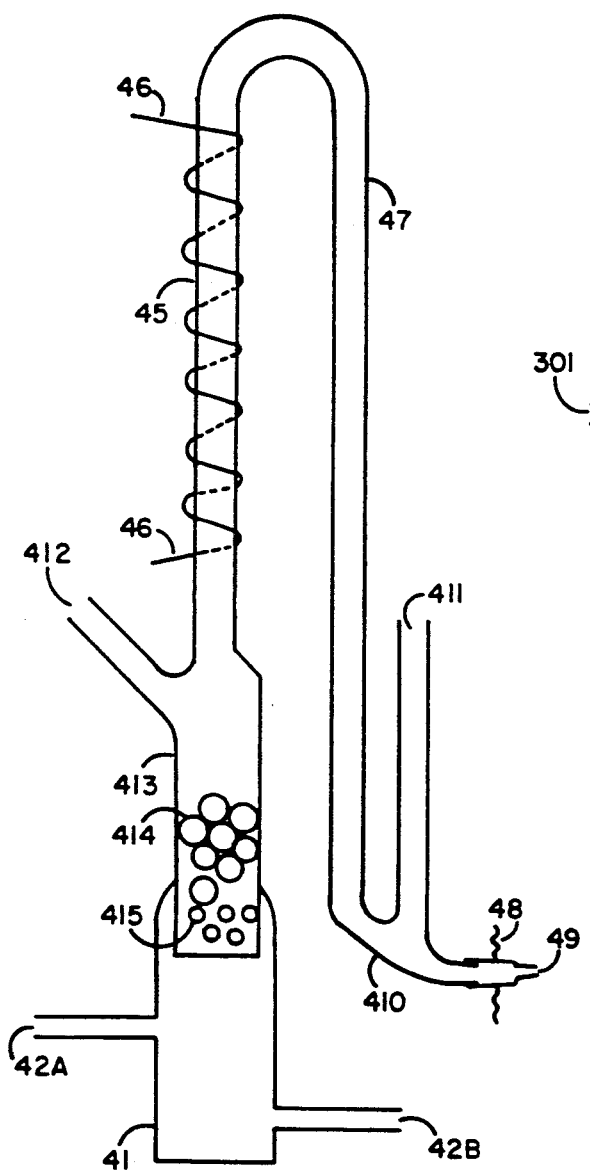
FIG. 3 is a schematic and simplified diagram of a third prior art apparatus for measuring volatile and/or steam distillable carbon compounds in water and also illustrating how such apparatus may be improved with this invention.
Figure 4:
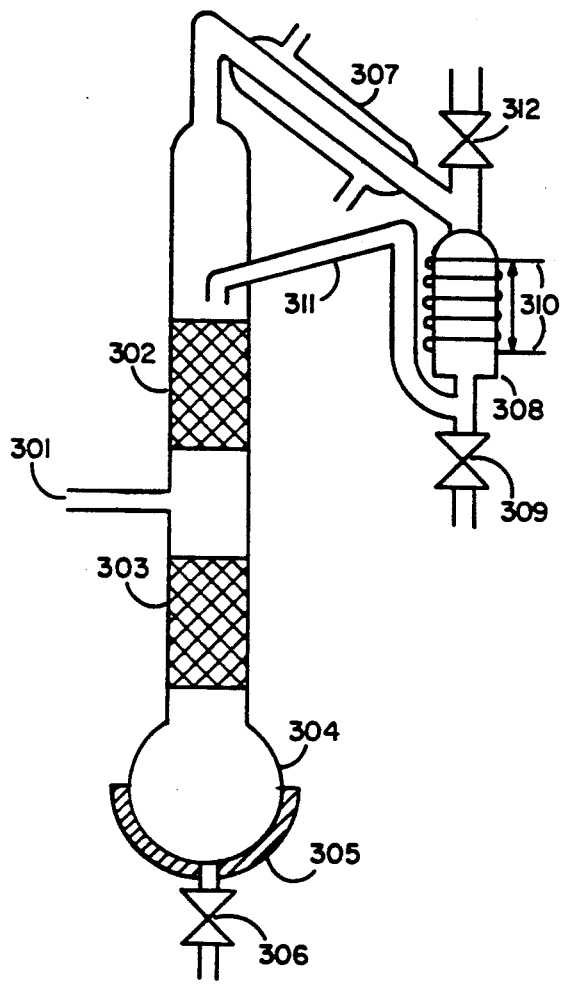
FIG. 4 is a schematic and simplified diagram of a preferred apparatus for measuring dissolved and/or dispersed carbon compounds in water and also illustrating how such apparatus may be improved in accordance with this invention.

The present invention pertains to apparatus and methods for measuring the concentration of carbon compounds (including halogenated carbon compounds) in water (particularly potable, pure and ultrapure water) comprising a reaction zone for converting such compounds to free and/or combined carbonic acid and/or free and/or combined low molecular weight organic acids (such free and/or combined carbonic acid and/or free and/or combined low molecular weight organic acids are referred to herein and in the appended claims as "carbonaceous acids"), means for contacting such carbonaceous acids in solution or in vapor phase with weakly basic anion exchange ("WBAX") resin in a suitable physical form and means for measuring the electrical impedance of such resin. According to some embodiments of this invention such carbonaceous acids are volatile and/or steam distillable.

Such WBAX resin may for example (without limitation) comprise:

copolymers of divinyl benzene, ethylene glycol dimethacrylate and/or other suitable crosslinking agent with dimethyl aminoethyl methacrylate, dimethyl amino ethyl acrylate, N-(dimethyl amino propyl) acrylamide, N-(dimethyl amino propyl) methacrylamide and/or other amino alkyl substituted acrylic esters or amides;

copolymers of one or more suitable crosslinking agents with styrene (and/or substituted styrenes such as vinyl toluene, ethyl vinyl benzene, alpha methyl styrene or a halo methyl styrene) which copolymers have been reacted to form or introduce halo methyl groups (if not already present) and subsequently converted to primary, secondary and/or tertiary amines with for example ammonia, methyl amine, dimethyl amine, ethylene diamine, propylene diamine, hydroxyethyl amine, di(hydroxyethyl)amine, diethylene triamine and the like;

copolymers (including block copolymers) of styrene (and/or substituted styrenes (as recited above) )with dienes (such as butadiene or isoprene) fabricated into suitable forms and vulcanized (for example with dicumyl peroxide) or cyclized (for example with solutions of titanium or aluminum chlorides in ether) which thus crosslinked copolymers have been subsequently reacted to form or introduce halomethyl groups if not already present and thereafter converted to primary, secondary and/or tertiary amines with ammonia or suitable amines such as those recited above;

suitable structure of film-forming polymers such as low density polyethylene (LDPE), linear low density polyethylene (LLDPE), high density polyethylene (HDPE), polyvinylidene fluoride (PVDF), polychlorotrifluoroethylene, polytetrafluoroethylene-coethylene, polychlorotrifluoroethylene-co-ethylene, poly-tetrafluoroethylene -co-hexafluoropropylene and the like which have been substantially saturated with styrene (and/or substituted styrenes such as alpha methyl styrene, vinyl toluene, ethyl vinyl benzene or a vinyl benzyl halide) optionally containing a crosslinking agent and perhaps a polymerization catalyst (such as benzoyl peroxide or azo-bis-isobutyronitrile), the imbibed monomers being subsequently polymerized by heat and/or gamma radiation for example, the resulting structures thereafter being reacted to form or introduce halomethyl groups (if not already present in at least some of the monomers utilized), the halomethyl groups being finally converted to primary, secondary and/or tertiary amine functions with ammonia or amines such as those recited above.

suitable structures of polyalkenes (such as polyethylene) which have been sulfochlorinated with sulfur dioxide and chlorine and subsequently reacted with diamines such as propylene diamine, N,N-dimethylpropylene diamine and the like.

crosslinked addition products of amines and epoxides.

crosslinked condensation products from reactants comprising one or more of formaldehyde, guanidine, amines, polyamines, phenol and substituted phenols.

WBAX resins prepared in accordance with U. S. Pat. Nos. 4,661,231; 4,711,907; 2,730,768; Re.24,865; 2,780,604; 2,860,097 and 2,800,445.

Figure 5:
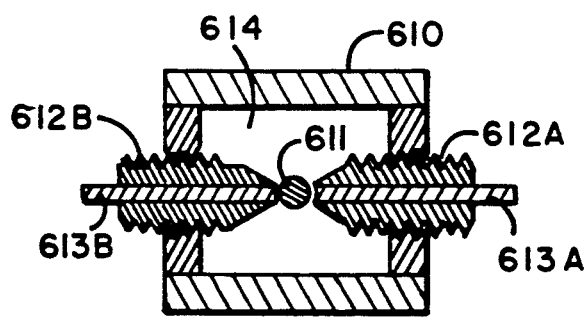
FIG. 5 is a schematic and simplified diagram of a preferred weak base anion exchange sensor for determining carbonaceous acids in water in conjunction with apparatus for oxidizing and/or reforming volatile and/or non volatile, dissolved and/or dispersed organic compounds in water to such carbonaceous acids.

Suitable structures include beads, strips, rods, fibers, hollow fibers, tubes, filaments, cubes (and other parallopipeds) including beds or masses of any of the above or mixtures thereof and any other structures which facilitate the measurement of electrical impedance. The structures may contain reinforcing fabrics or fibers or interpolymers such as PVC or PE. The structures may be asymmetric, i.e. the WBAX region may be substantially only on one or more of the surfaces of the structure. Related structures for measuring the concentration of carbon dioxide in air are described in U.S. Pat. No. 3,558,279 incorporated herein by reference. One suitable structure is represented schematically in FIG. 5 (not to scale) in which 611 represents a bead of weakly basic anion exchange resin typically about 0.05 cm in diameter. The bead is held between two electronically conducting probes 613a and 613b which may be of any suitable material for example graphite, an electronically conducting ceramic (e.g. a doped titanium dioxide) or an electronically conducting metal such as titanium. For the sake of clarity the probes 613a and b are shown as not contacting bead 611 although in actual use the faces of probes 613a and b adjacent to bead 611 are in firm contact with bead 611. Such faces are preferably coated with a thin film of a noble metal such as platinum, palladium, gold or iridium, or other coating providing a low resistance interface with bead 611. Probes 613a and b may be imbedded in any suitable electrically insulating material 612a and 612b which are in turn mounted in a holder or vessel 610 having an accessible cavity 614. Insulators 612a and b are both shown as threaded and fitting into female threads in holder 610 in order to provide firm contact of probes 612a and b with bead 611. Obviously only one of 612a and b need be threaded, the other fitting permanently (or at least by a tight fit) inserted into holder 610. Alternatively probes 613a and/or b may be pressed against bead 611 by means of one or more springs.

The WBAX may be regarded as insoluble but hydrated compounds of the general formula: -RNR$_2$HOH where -R represents the substrate polymer including any tether to said polymer and the R* may be independently selected from the group consisting of H, alkyl groups such as methyl, ethyl, propyl, substituted alkyl groups such as benzyl, aminoalkyl, alkylamino alkyl, hydroxy alkyl and the like. The WBAX may also be regarded as dissociating according to the reaction:

$$-R\,NR_2HOH = -RNR_2H^{30} + OH^-\text{ with an ionization constant}$$

described as:

$$K_B = \frac{(-RNR_2{}^*H^+)(OH^-)}{(-RNR_2{}^*HOH)}$$

where $(-RNR_2H^{30})$, $(OH^-)$, $(-RNR_2HOH)$ may be expressed in any convenient units e.g. gram-mols (or gram-equivalents) per kilogram of water contained within the WBAX resin structure. The quantities (...) are preferably corrected for any reinforcing medium. Regardless of the concentration units used, WBAX useful in this invention will generally have $K_B$'s in the range of from about $10^{-3}$ to about $10^{-8}$. The quantity $(-RNR_2H^+)+(-RNR_2HOH)$ is generally called the ion exchange (IX) capacity of the WBAX resin. The ionization constants of ion exchange materials are only roughly "constant", decreasing with the degree of ionization of the fixed, charged groups.

The carbonaceous acids formed from organic matter in water according to this invention may be regarded as having the general formula: R'COOH where R'may be H, OH, HOOC or an organic residue. The carbonaceous acid may be regarded as dissociating according to the reaction:

$$R'COOH = R'COO^- + H^+ \text{ with an ionization constant described}$$

as:

$$K_A = \frac{(R'COO^-)(H^+)}{(R'COOH)}$$

where $(R'COO^{31})$, $(H^+)$, $(R'COOH)$ in aqueous solution may also be expressed as gram-mols (or gram-equivalents) per kilogram of water. $K_A$'s will also generally be in the range of from about $10^{-3}$ to about $10^{-8}$ in appropriate units. Among the carbonaceous acids, as herein defined, carbonic acid is capable of ionizing in two stages, first to bicarbonate anion and secondly to carbonate anion. When an aqueous solution of (low molecular weight) carbonaceous acid and a WBAX are in mutual contact, the undissociated carbonaceous acid and its dissociation products will diffuse into the WBAX until an equilibrium is reached both in the resin phase and between the resin and solution phases. $(-RNR_2HOH$ and $-RNR_2H^+$ are of course both bound to the WBAX structure and are not free to migrate into the solution phase). The equilibrium in the WBAX resin phase may be described by the expression:

$$-RNR_2HOH + R'COOH - RNR_2H^+ + R'COO-$$

and the quilibrium constant:

$$K_R = \frac{(-RNR_2{}^*H^+)(R'COO^-)}{(-RNR_2{}^*HOH)(R'COOH)}$$

$K_R$ must be equal to $\dfrac{K_A K_B}{K_w}$ where $K_w=(OH^-)(H^+)$. The $K_R$, $K_A$, $K_B$ and $K_w$ in the previous sentence are strictly speaking those that apply in the WBAX resin phase but the values of $K_A$ and $K_w$ in the resin phase will not be far different from those applying in the solution phase. Further the concentration of (unionized) R'COOH will not differ greatly between the resin and solution phases and the product $(R'COO-)(H^+)$ will not differ greatly between the resin and solution phases. By way of example the following table may be estimated for carbonic acid assuming:

the first ionization constant of carbonic acid is $4.3 \times 10^{-7}$ mols/kg water the second ionization constant of carbonic acid is $5.6 \times 10^{-11}$ mols/kg water the ion product of water is $10^{-14}$ (mols/kg water)$^2$ the total capacity $(-RNR^*{}_2 + -RNR^*{}_2H)$ of the WBAX is 4 mols/kg water and where:

$pK^*{}_B$ is the negative logarithm to the base 10 of the ionization constant of the WBAX in the fully free base form in mols/kg water $K_B = K^*{}_B \exp(-3.9(-RNR^*{}_2)^{\frac{1}{2}})$ $(C0_2)_s$ is the initial total concentration in micrograms of $CO_2+HCO_3{}^-+CO_3{}^2$ in 1 cm$^3$ of water expressed as $CO_2$ the "conductance of a 0.05 cm bead" is that of a bead having 50% water content by volume, the $pK^*{}_B$ listed and in equilibrium with 1 cm$^3$ of the initial $(CO_2)_s$ solution and is expressed in microSiemens ($\mu S$).

| $pK^*{}_B$ | Initial Concentration $(CO_2)_s$ total, $\mu g/g$ | Conductivity of 1 ml Initial Concentration | Conductance of 0.05 cm bead |
|---|---|---|---|
| 3.2 | 1 | 1.4 $\mu S$ | 92 $\mu S$ |
| 3.2 | 0.1 | 0.7 | 66 |
| 4.8 | 1 | 1.2 | 22 |
| 4.8 | 0.1 | 0.4 | 14 |
| 6.2 | 1 | 1.1 | 5 |
| 6.2 | 0.1 | 0.4 | 2.6 |

The above table assumes that the $CO_2$ is absorbed in water having a specific conductance of not more than about 10% of the conductance of the 1 ml aliquot of the solution of $CO_2$ in water. As mentioned above about 1 ppm NaCl already has a specific conductivity of about 2$\mu S$ per cm$^3$. Hence almost any carry-over of strongly ionized electrolytes affects the significance of the conductivity measurement of the water containing dissolved $CO_2$. However even in the absence of any Donnan exclusion of NaCl from the WBAX sensor, 1 ppm of NaCl in the ambient solution will contribute only about 0.005$\mu S$ to the conductance of the 0.05 cm bead assumed in the example above. As the WBAX becomes ionized by sorption of $CO_2$ NaCl will be increasingly excluded and the contribution to conductance by NaCl will become even less. Chloride and bicarbonate will of course attain an anion exchange equilibrium which should not show any substantial preference for either ion. In any case the mobility of chloride and bicarbonate in the WBAX are substantially equal so the effect of any exchange will be small. Chloride and carbonate anions will also attain an exchange equilibrium. In this case, owing to the higher charge of the carbonate ion, the WBAX will highly prefer carbonate.

As shown by the above definition of $K_R$ and reflected by the above table, the WBAX will tend to maintain equilibrium with the ambient concentration of carbonaceous acid as the latter changes up or down. The rate of attainment of such new equilibrium will depend of course inter alia on the extent of deviation from the previous equilibrium and on the ratio of the area of the WBAX structure to its volume. Alternatively the WBAX resin sensor can be regenerated to the substantially free base form after any or each measurement of the quantity of organic matter in water. For example it can be contacted automatically with a dilute alkaline earth or alkali metal hydroxide solution and then with ultrapure water. According to a preferred embodiment the WBAX resin sensor is regenerated substantially to the free base form continuously or after any or each measurement of organic matter by passing through it a substantially direct electric current. "Substantially direct" implies that the direct current may have a substantial ripple or alternating current component and/or may have its direction of passage reversed symmetrically or asymmetrically from time to time e.g. after each or after several measurements of organic matter. "Substantially direct" also implies that an alternating current may be impressed to measure the conductance of the WBAX and simultaneously a direct current impressed tending to cause its regeneration to the free base form. Such simultaneous application of alternating and direct currents permits rapid continuous measurement of carbonaceous acids. The conductance of an audio frequency alternating current is not substantially affected by decomposition potentials at the electrodes contacting the WBAX for the purpose of measuring its conductance.

Figure 6:
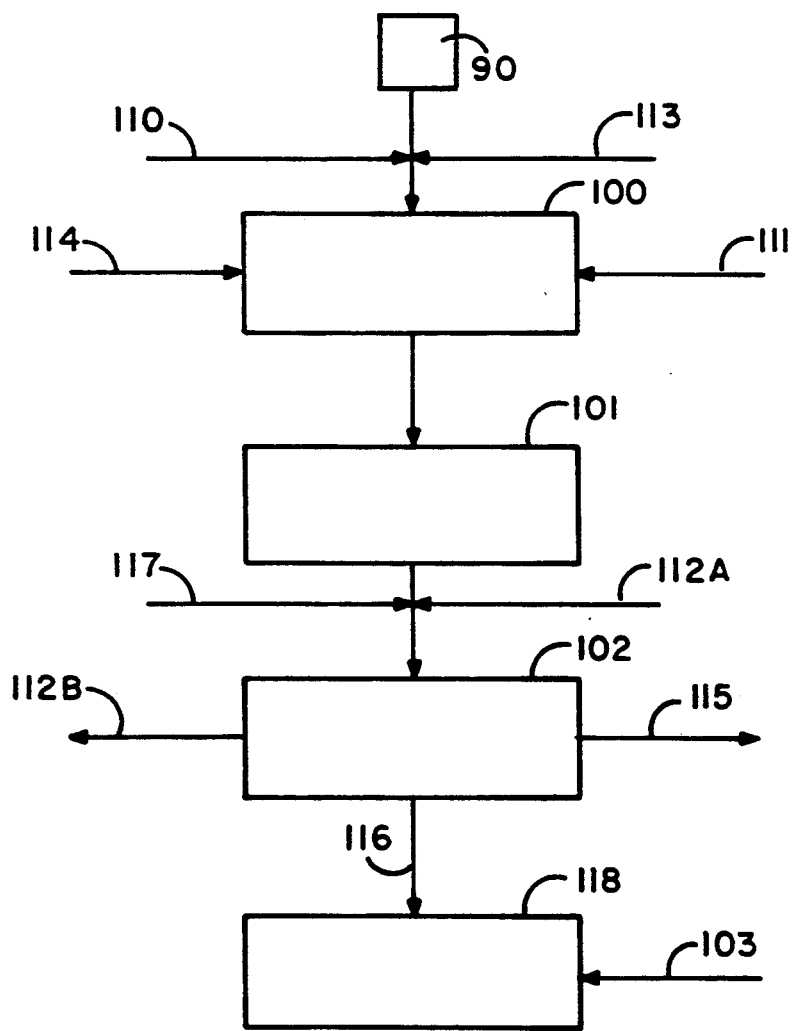
FIG. 6 is a simplified flow sheet of a preferred apparatus and process according to this invention.

Referring to FIG. 6, a preferred apparatus and method are briefly as follows:

a) A sample of water 90 containing carbon compounds which, with or without natural oxidants (e.g. oxygen) or added oxidants is introduced into an oxidation/reforming zone 100. Additional oxidants may be introduced into the sample before the oxidation/reforming zone e.g. by optional means 113 and/or directly into such zone, e.g. by optional means 114. The pH may be adjusted and/or controlled for various purposes by addition of suitable acids, alkalies or buffers to the sample before the oxidation zone e.g. by optional means 110 and/or directly into such zone e.g. by optional means 111.

If the oxidant added to the sample is for example an excess of oxygen or air or if the reactions in the oxidation zone give rise to gases other than carbon dioxide and water (which could reduce the sensitivity or precision of the subsequent measurement of carbonaceous acids by means of a weak base anion exchanger) then such excess or formed gases can be removed in an optional gas/liquid separator 101. In such gas the influent sample to the separator should preferably have a pH greater than about 8.5 at which pH about 99% of the carbon dioxide is present as bicarbonate and will not be appreciably lost.

With or without gas-liquid separation the oxidized sample is sent to a carbonic acid fractionator 102. Reductants may be introduced into the sample before the carbonic acid fractionator 102 by optional means 117. The pH may be adjusted and/or controlled by addition of the appropriate chemical to the sample before the fractionator 102 by optional means 112a or directly into the fractionator by optional means 112b. A fraction depleted in carbonic acid (and volatile organic acids) is withdrawn from the fractionator 102 by means 115 and a fraction enriched in carbonic acid (and volatile organic acids) is withdrawn by means 116. The carbonic acid content of the enriched fraction is determined by measuring the conductivity of weakly basic anion exchange resin structure 118 by electrical impedance measurement means 103. The sample in the fractionator preferably has a pH less than about 4.5 at which pH about 99% of the carbon dioxide is present as carbonic acid.

In oxidation zone 100 any suitable oxidant can be used. Preferred are oxidants which react rapidly in the liquid phase below the boiling point of water. Examples include without limitation:

Inorganic peroxy or superoxy compounds, e.g. persulfates (i.e. peroxydisulfates) at temperatures in the range of from about 90° to about 100° C.;

Catalyzed inorganic peroxide, e.g. Fenton's reagent, a mixture of hydrogen peroxide and ferrous salt (or other "one-electron" inorganic catalysts such as cuprous salts), a particularly good source of the powerfully oxidizing hydroxyl radical (Proc. Chem. Soc. 9, 113 (1893). Another example is a mixture of a ferrous or silver salt and a peroxydisulfate salt;

Inorganic peroxides, e.g. hydrogen peroxide, peroxy disulfates, peroxymonosulfuric acid (Caro's acid), peroxy monophosphoric acid, potassium peroxydi-phosphate, sodium pyrophosphate peroxyhydrate, perborates, sodium carbonateperoxyhydrate or peroxymonocarbonate, oxone peroxymonosulfate, sodium peroxide, potassium superoxide and the like, without or without added inorganic acid such as phosphoric or sulfuric acid, promoted with the 185 nm line of a mercury arc lamp or by a suitable line from a U.V. laser, e.g. a tunable U.V. laser such as a tunable excimer laser.

Oxygen promoted by U.V. light, e.g. the 185 nm line of the mercury arc lamp. (Water is apparently also converted to hydroxyl free radicals by such line but it is a convention in the U.V. radiation art that such radicals are subsumed under those derived from oxygen in the same system).

Hydrogen peroxide (or other inorganic peroxy compound) plus ozone, ozone alone or ozone promoted by U.V. light.

Suitable U.V. sources for purposes of this invention include any which produce a substantial amount of radiation characterized by being substantially transmitted by quartz or vitreous silica and by promoting the oxidation of organic compounds by oxygen, peroxides and/or ozone. Such radiation should generally be in the range of from about 166 nm to about 330 nm the preferred range depending upon the oxidant used. For example in the case of oxygen the range may be from about 166 nm to about 250 nm.

The small quantities of ozone required may be generated electrolytically as well known in the art.

While the invention has been described with respect to certain exemplifications and embodiments thereof, the scope is not to be so limited except as in the claims appended hereto.

I claim:

1. Apparatus for estimating the concentration of carbon compounds in water comprising means for converting such compounds at least in part to one or more carbonaceous acids, means for contacting at least part of such one or more carbonaceous acids in solution and in vapor phase with a body comprising weakly basic anion exchange resin and means for measuring the electrical impedance of at least part of said resin.

2. Apparatus according to claim 1 in which said resin has an ionization constant in substantially the free base form in the range of from about $10^{-3}$ to about $10^{-8}$ gram moles per kilogram of imbibed water.

3. Apparatus according to claim 1 in which said body comprises one or more structures having weakly basic anion exchange resin substantially in one or more of the surfaces of said structures.

4. Apparatus according to claim 1 in which said means for converting said carbon compound at least in part to one or more carbonaceous acids comprises a first heated zone, means for introducing at least a portion of said water into said first heated zone, means for evaporating without substantial carry-over of droplets, mist and spray at least part of the water in the first heated zone and passing the vapor into and through a second heated zone, means for maintaining the temperature of said second heated zone in the range of from about 450 to about 1000° C., and in which said means for contacting at least part of said one or more carbonaceous acids in solution and in vapor phase with a body comprising weakly basic anion exchange resin comprises means for collecting and condensing water vapor from said heated zone to condensed liquid water and means for contacting at least a portion of such condensed liquid water with said body comprising weakly basic anion exchange resin.

5. Apparatus according to claim 1 in which said means for converting such compounds at least in part to one or more carbonaceous acids comprises at least one source of ultraviolet irradiation to convert at least in part said carbon compounds to carbonaceous acids in which said means for contacting such one or more carbonaceous acids in solution and in vapor phase with a body comprising weakly basic anion exchange resin comprises sparging means for sparging at least part of said one or more carbonaceous acids out of said means for converting such compounds at least in part to one or more carbonaceous acids into a volume of water and means for contacting at least a portion of said volume with said body comprising weakly basic anion exchange resin.

6. Apparatus according to claim 1 in which said means for converting said carbon compounds at least in part to one or more carbonaceous acids is a liquid phase reaction zone and in which said apparatus includes means for evaporating without substantial carry-over of droplets, mist, and spray at least part of the water from said liquid phase reaction zone to evaporated water, means for collecting and condensing at least part of said evaporated water to condensed liquid water and in which said means for contacting such one or more carbonaceous acids with a body comprising weakly basic anion exchange resin comprises means for contacting at least a portion of said condensed liquid water with said body.

7. Apparatus according to claim 6 in which said means for evaporating without substantial carry-over of droplets, mist, and spray includes means for condensing and refluxing at least part of said evaporated water.

8. Apparatus according to claim 1 including means for regenerating said resin substantially to the free base form.

9. Apparatus according to claim 8 in which said means for regenerating said resin substantially to the free base form comprises means for passing a substantially direct electric current through said resin.

10. Apparatus according to claim 8 in which said means for regenerating said resin substantially to the free base form comprises means for substantially continuously passing a substantially direct electric current through said resin.

* * * * *